United States Patent [19]
Zoghbi et al.

[11] Patent Number: 6,121,454
[45] Date of Patent: *Sep. 19, 2000

[54] SYNTHESIS OF PHARMACEUTICALLY USEFUL PYRIDINE DERIVATIVES

[75] Inventors: Michel Zoghbi; Liquin Chen, both of Richmond Hill, Canada

[73] Assignee: PDi-Research Laboratories, Inc., Richmond Hill, Canada

[*] Notice: This patent issued on a continued prosecution application filed under 37 CFR 1.53(d), and is subject to the twenty year patent term provisions of 35 U.S.C. 154(a)(2).

[21] Appl. No.: 09/063,001

[22] Filed: Apr. 21, 1998

[30] Foreign Application Priority Data

May 6, 1997 [CA] Canada .................................. 2204580

[51] Int. Cl.[7] ...................... C07D 213/61; C07D 213/62; C07D 213/72
[52] U.S. Cl. .................. 546/245; 546/273.4; 546/273.7; 546/290; 546/303; 546/310; 546/312; 546/345
[58] Field of Search ...................................... 546/290, 303, 546/310, 34, 312, 344, 345, 273.7, 273.4

[56] References Cited

U.S. PATENT DOCUMENTS

| | | | |
|---|---|---|---|
| 3,519,717 | 7/1970 | Symchowicz et al. | 546/345 |
| 4,544,750 | 10/1985 | Brandstrom et al. | 546/290 |
| 4,620,008 | 10/1986 | Brandstom et al. | 546/271 |
| 4,672,125 | 6/1987 | Gray et al. | 546/345 |
| 5,061,805 | 10/1991 | Goe | 546/349 |
| 5,066,810 | 11/1991 | Baumann | 546/300 |
| 5,374,730 | 12/1994 | Slemon et al. | 546/271 |
| 5,386,032 | 1/1995 | Brandstrom et al. | 546/271 |
| 5,510,090 | 4/1996 | Cuillerdier et al. | 546/169 |

FOREIGN PATENT DOCUMENTS

| | | |
|---|---|---|
| 1127158 | 7/1982 | Canada . |
| 1234118 | 3/1988 | Canada . |
| 1263119 | 11/1989 | Canada . |
| 0 103 553-B1 | 3/1984 | European Pat. Off. . |
| 0 103553-A1 | 3/1984 | European Pat. Off. . |
| 0176308 | 4/1986 | European Pat. Off. . |
| 0226558 | 6/1987 | European Pat. Off. . |
| 0446961 | 9/1991 | European Pat. Off. . |
| 0 484 265 | 5/1992 | European Pat. Off. . |
| 0533131 | 3/1993 | European Pat. Off. . |
| 29611 | 5/1965 | Germany . |

OTHER PUBLICATIONS

Chou, S.Y., et al., "Synthesis of 2—Hydroxymethyl–3,5–Dimethyl–4–Methoxypyridine: A Key Intermediate for Omeprazole", *Heterocylces*, vol. 45, No. 1, 1997, pp. 77–85.

Kohl, B., et al., "AATPase Inhibiting 2–[(2–Pyridylmethyl)sulfinyl]benzimidazoles. 4.[1] A Novel Series of Dimethoxypyridyl–Substituted Inhibitors with Enhanced Selectivity. The Selection of Pantoprazole as a Clinical Candidate", *J. Med. Chem.* 1992, 35, pp. 1049–1057.

Crowe, A.M., et al., "The Preparation of $^{14}$C, $^{35}$S and [13]C Labelled Forms of Omeprazole", *Journal of Labelled Compounds and Radiopharmaceuticls*, vol. XXIII, No. 1, pp. 21–33.

Weidmann, K., et al., 2–[(2–Pyridylmethyl)sulfinyl]–1H–thieno[3,4–d]imidazoles. A Novel Class of Gastric H+/K+–ATPase Inhibitors, *J. Med. Chem.*, 1992, 35, 438–450.

Bernardi, R., et al., "Nucleophilic Character of Carbon Free Radicals. A New Convenient, Selective Carboxylation of Heteroaromatic Bases", *Tetrahedron Letters No. 9*, 1973, pp. 645–648.

Minisci, F., et al., "Recent Developments of Free–Radicals Substitutions of Heteroaromatic Bases", *Heterocycles*, vol. 28, No. 1, 1989, pp. 489–519.

Minisci, F., "Novel Applications of Free–Radicals Reactions in Preparative Organic Chemistry", *Synthesis*, Jan., 1973, pp. 1–24.

Minisci, "Novel Applications of Free–Radical Reactions in Preparative Organic Chemistry", *Synthesis*, No. 1, 1973, pp. 1–24.

Bernardi et al., "Nucleophilic character of carbon free radicals. A new convenient, selective carboxylation of heteroaromatic bases.", *Tetrahedron Letters*, vol. 9, 1973, pp. 645–648.

Fontana, et al., "Homolytic acylation of protonated pyridines and pyrazines with alpha–keto acids: the problem of monoacylation", *J. Org. Chem.*, vol. 56, 1991, pp. 2866–2869.

(List continued on next page.)

*Primary Examiner*—D. Margaret Seaman
*Attorney, Agent, or Firm*—Ivor M. Hughes; Marcelo K. Sarkis; Neil H. Hughes

[57] ABSTRACT

A process is provided for the preparation of compounds of formula I,

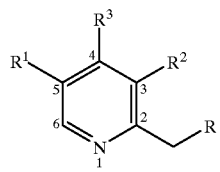

useful in the preparation of compounds such as Omeprazole, Lansoprazole and Pantoprazole, wherein $R^1$=H or $CH_3$, $R^2$=H or $CH_3$, $R^3$=Alkoxy (1–4C), $OCH_2CF_3$, Cyano, Hydrogen, Halogen, Acetoxy or Aryloxy, any electron withdrawing group or salts (organic or inorganic) of electron donating groups, R=Alkoxy, Hydroxy, Halogen, Activated ester, Tosylate, Mesylate, Thiol or Xanthyl, wherein the process for the preparation of compound of formula I employs a free radical reaction to functionalize the 2-position.

29 Claims, No Drawings

OTHER PUBLICATIONS

Citterio, et al., "Nucleophilic character of the alkyl radicals. 19. Absolute rate constants in the homolytic alkylation of protonated heteroaromatic bases by n–butyl and tert.–butyl radicals.", *J. Org. Chem.*, vol. 45, 1980, pp. 4752–4757.

Database WPI Section Ch, Week 9250 Derwent Publications Ltd., London, GB; AN 92–412945 & KR 9 109 817 B (Choong–Wae Pharm. Co.), 1991.

Chou, et al., "Synthesis of 2–hydroxymethyl–3, 5–dimethyl–4–methoxypyridine: a key intermediate for omeprazole", *Heterocycles*, vol. 45, No. 1, 1997, pp. 77–85.

Database WPI Section Ch, Week 7406 Derwent Publications Ltd., London, GB; AN 74–10791V & SU 330 737 A (N–Caucasus Phytopath), 1974.

Chemical Abstracts, vol. 51, No. 12, Jun. 25, 1957, Columbus, Ohio, US; Jerchel, et al., "Synthesis with pyridylpyridium halides . . . ", col. 8737.

Epsztajn, et al., "Application of Organolithium and Related Reagents in Synthesis. Part 9[1],. Synthesis and Metallation of 4–Chloropicolin– and 2–Chloroisonicotin–Anilides. A Useful Method for Preparation of 2,3,4–Trisubstituted Pyridines", *Tetrahedron*, vol. 47, No. 9, 1991, pp. 1697–1706.

Epsztajn, et al., "Application of Organolithium and Related Reagents in Synthesis Part 7[1],. Synthesis and Metallation of 4–Methoxypicolin– and 2–Methoxyisonicotin–Anilides. A Useful Method for Preparation of 2,3,4–Trisubstituted Pyridines",*Tetrahedron*, vol. 45, No. 23, 1989, pp. 7469–7476.

Chu, et al., "Toward the Design for an RNA:DNA Hybrid Binding Agent", *J. Am. Chem. Soc.*, vol. 116, 1994, pp. 2243–2253.

Godard, et al., "Synthesis of new substituted quinolizidines as potential inhibitors of ergosterol biosynthesis", *Tetrahedron*, vol. 51, No. 11, 1995, pp. 3247–3264.

Chemical Abstracts 121:35276, Kiselyov, Heterocycles, vol. 38(2), pp. 259–262, 1994.

Chemical Abstracts 120:322835, Huang, 1993.

chemical Abstracts 113:15227, Huang, 1990.

Chemical Abstracts 105:60499, Naumann, 1985.

Chemical Abstracts 127:190912, El–Bardan, 1997.

Chemical Abstracts 124:176004, Chbani, 1995.

Chemical Abstracts 124:105608, Lagorce, 1995.

Chemical Abstracts 111:7405, Lang, 1989.

Russell, chemical abstracts 111:133919, 1989.

Minisci, Chemical Abstracts 105:208247, 1986.

Russell, Chemical Abstracts 103:104823, 1985.

Minisci, Chemical Abstracts 70:28123, 1968.

SYNTHESIS OF PHARMACEUTICALLY USEFUL PYRIDINE DERIVATIVES

FIELD OF INVENTION

This invention relates to the manufacture of intermediates suitable for use in the manufacture of Omeprazole and other medicines and the use thereof to manufacture Omeprazole and other medicines. This invention in its broadest aspects is directed to the manufacture of intermediates useful in the manufacture of medicines such as Omeprazole, Pantoprazole, and Lansoprazole, intermediates suitable for the use to manufacture medicines and the processes for manufacturing the intermediates and for using those intermediates to manufacture medicines.

BACKGROUND OF INVENTION

The reported synthesis of Omeprazole basically involves the coupling of intermediates A and B to form intermediate C which is oxidized to the sulfinyl or sulfoxy compound, Omeprazole.

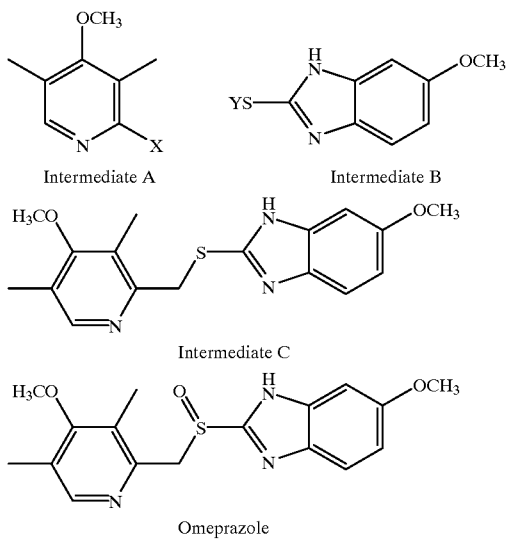

(See for example Canadian Letters Patent No. 1,127,158 Hassle)

Hassle used the N-oxide form of intermediate A:

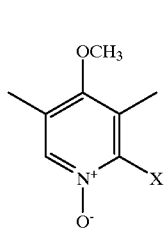

(See Canadian Letters Patent No. 1,234,118)

The N-Oxide form may be considered necessary to prepare the precursor 4-nitro compound and it is essential for the alkylation/functionalization of the 2-position (X), according to Hassle's process. Intermediate A (N-Deoxygenated) is then coupled with intermediate B on the route to Omeprazole.

Esteve, on the other hand, described a synthesis that involves coupling the N-oxides of the 4-nitro or the 4-Chloro with intermediate B to form the N-Oxide of intermediate C. Following that, Esteve either substituted at the pyridinyl 4-position with the methoxy and then reduced the N-Oxide or vice-versa.

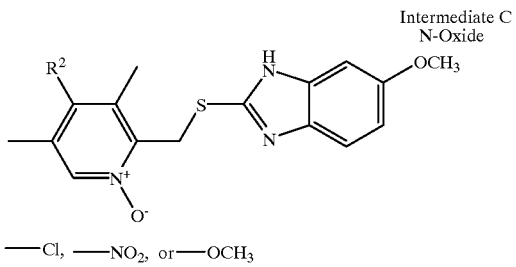

$R^2$: —Cl, —$NO_2$, or —$OCH_3$ (See European Patent No. 484,265)

Torcan, reported a method that offers advantages involving the oxidation and the purification of the final product. Their method comprises oxidizing the amide of Intermediate C to the corresponding amide sulfinyl compound followed by hydrolysis and decarboxylation to form Omeprazole. Torcan did not report processes for the manufacture of the pyridinyl moiety.

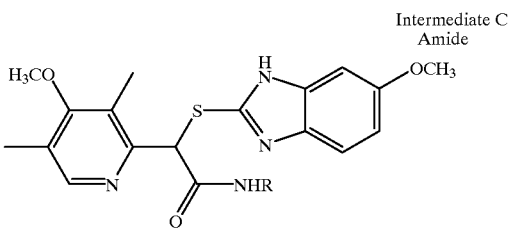

(See U.S. Pat. No. 5,374,730)

Other Oxidation methods used for converting the thioether "Intermediate C" to the sulfinyl are purportedly taught by recent Takeda (CA 1,263,119) and Hassle's (U.S. Pat. No. 5,386,032) patents.

C. L. Pharma's U.S. Pat. No. 5,066,810 teaches a process to manufacture

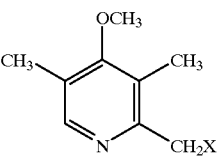

where X is OH or Cl by catalytic hydrogenation of 3,5-dimethyl-4-methoxy-2-cyanopyridine as depicted below

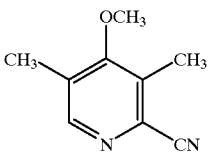

in the presence of an inert diluent, the resulting 3,5-dimethyl-4-methoxy-2-aminomethylpyridine as depicted below

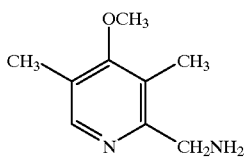

which is then reacted with sodium nitrite in aqueous-acidic solution to give 3,5-dimethyl-4-methoxy-2-hydroxymethylpyridine and ultimately reacting the latter with thionyl chloride to give 3,5-dimethyl-4-methoxy-2-chloromethylpyridine.

In European Patent Publication No. 0103553 and in Canadian Letters Patent 1,234,118 and in U.S. Pat. Nos. 4,544,750 and 4,620,008, the following synthetic route for the pyridine part of omeprazole is described:

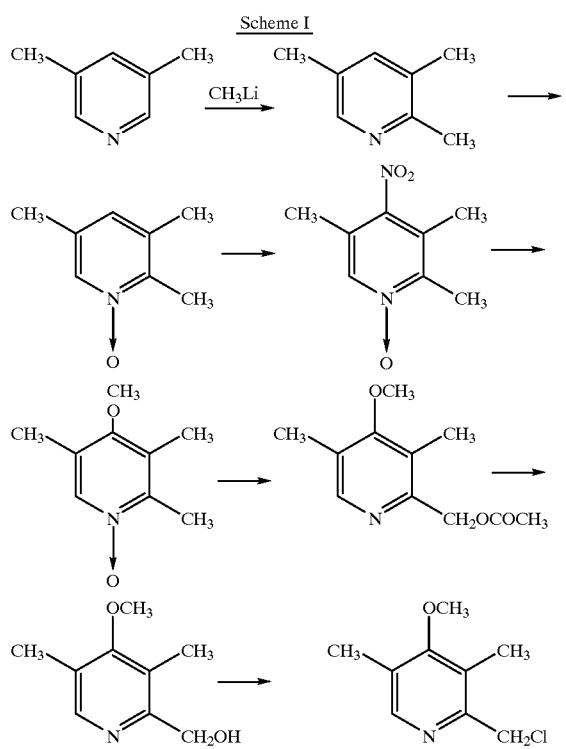

More recently, a method for the synthesis of intermediate A was published by a Taiwanese group. This procedure consisted of preparation of a the pyrone, pyridone and pyridine derivatives that can be converted to intermediate A. (Heterocycles, 45,1997, 77).

There are certain disadvantages associated with the current manufacturing processes, largely derived from the N-Oxide intermediates. Nitropyridines and their N-oxides are suspected carcinogens and therefore are unsafe to handle. Also, the above processes employ the nitropyridines and their N-oxides in the early or late stages of the manufacture. In both cases the suspected carcinogens are potential impurities.

While the Taiwanese method does not employ nitropyridines or N-oxides, it suffers from the disadvantage that it employs a large number of steps (approximately 10 steps) and the low availability of the starting material. Both are factors that affect the manufacturing yield and cost.

It is therefore an object of the invention to provide a method of manufacturing intermediates useful in preparing medicines where said intermediates avoid N-oxides that are suspected carcinogens.

It is also another object of the invention to provide methods of manufacturing intermediates useful in preparing medicines where said method employs intermediates that are safe to handle.

It is also another object of the invention to provide methods of manufacturing intermediates useful in preparing medicines wherein the number of steps are minimal in number.

It is also another object of the invention to provide methods of manufacture which incorporate materials that are readily available.

Further and other objects of the invention will be realized by those skilled in the art from the following summary of the invention.

SUMMARY OF THE INVENTION

According to one aspect of the invention, there is provided a process of making Compound III (a shown hereafter) by reacting a compound of the formula II

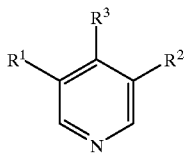

II with an organic free radical a radical • $R^4$ to produce the compound of formula III

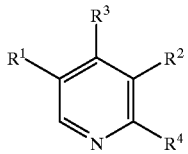

III wherein $R^1$=H or $CH_3$ $R^2$=H or $CH_3$ $R^3$=Alkoxy (1–4C), $OCH_2CF_3$, Cyano, Hydrogen, Halogen, Acetoxy or Aryloxy, any electron withdrawing group or salts (organic or inorganic) of electron donating groups $R^4$=Alkyl, Acyl (ketone), Amides (carbamoyl), Alkoxycarbonyl ($COOR^1$, $R^1$=(1–3C)), Aryloxycarbonyl, Carboxylic Acid, Phenoxymethyl, Hydroxymethyl or an obvious chemical equivalent. (The source of $R^4$ may be any suitable compound.)

According to another aspect of the invention, there is provided a process of producing a compound of formula I'

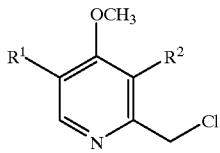

I' using intermediate III. An exemplary process may be by carrying out the following reaction step or steps which are obvious chemical equivalents of the following steps:

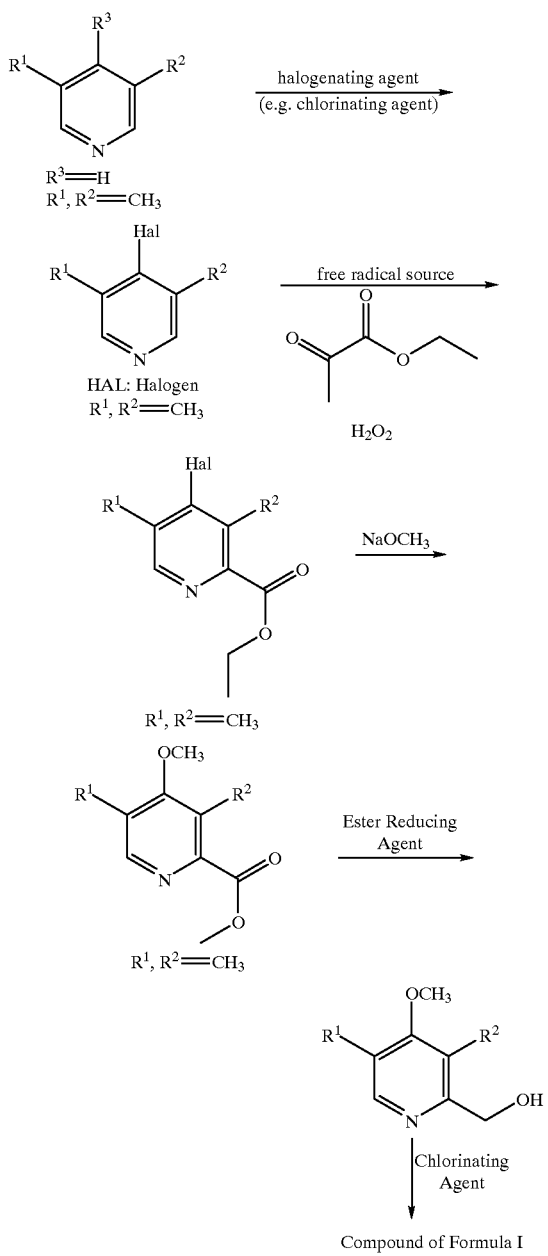

According to another aspect of the invention, there is provided a process of manufacturing Omeprazole by using the intermediate formed by the process above described with the appropriate substituents or an obvious chemical equivalent.

According to another aspect of the invention, there is provided a process of manufacturing Pantoprazole by using the intermediate formed by the process above described with the appropriate substituents or an obvious chemical equivalent.

According to another aspect of the invention, there is provided a process of manufacturing Lansoprazole by using the intermediate formed by the process above described with the appropriate substituents or an obvious chemical equivalent.

According to another aspect of the invention, there is provided a process of forming a compound having the structure

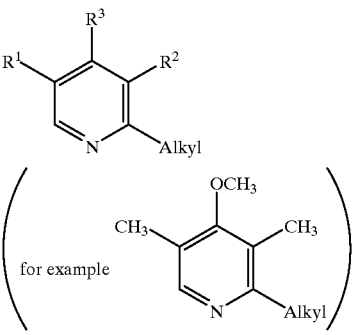

by reacting a compound having the structure

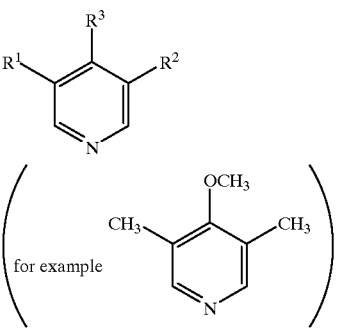

$R^1$, $R^2$ and $R^3$ as previously defined, with a radical • alkyl under free radical reaction conditions or an obvious chemical equivalent.

According to another aspect of the invention, there is provided a process of forming a compound having the structure

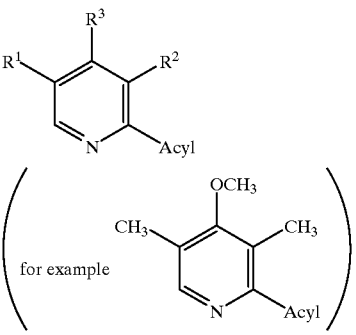

by reacting a compound having the structure

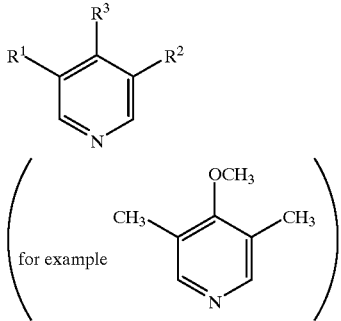

$R^1$, $R^2$ and $R^3$ as previously defined, with a radical • acyl under free radical reaction conditions or obvious chemical equivalent.

According to another aspect of the invention, there is provided a process of forming a compound having the structure

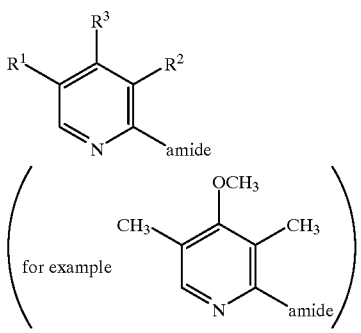

by reacting a compound having the structure

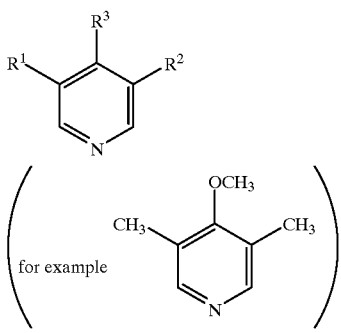

$R^1$, $R^2$ and $R^3$ as previously defined, with a radical • amide under free radical reaction conditions or obvious chemical equivalent.

According to another aspect of the invention, there is provided a process of forming a compound having the structure

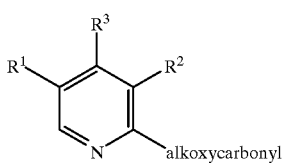

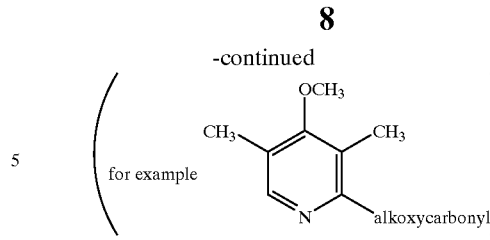

by reacting a compound having the structure

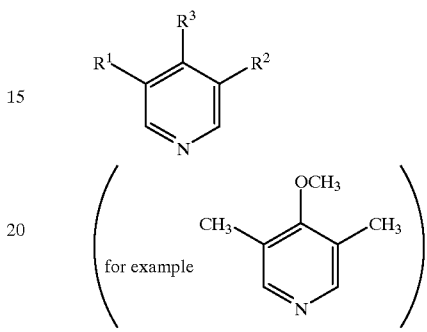

$R^1$, $R^2$ and $R^3$ as previously defined, with a radical • alkoxycarbonyl under free radical reaction conditions or obvious chemical equivalent.

According to another aspect of the invention, there is provided a process of forming a compound having the structure

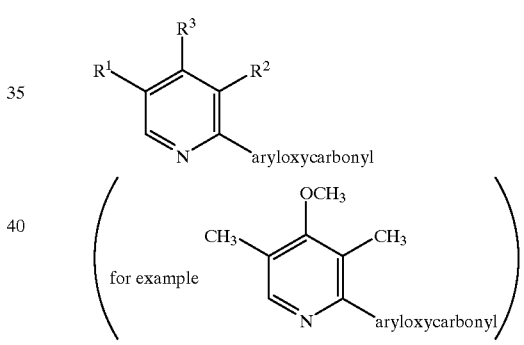

by reacting a compound having the structure

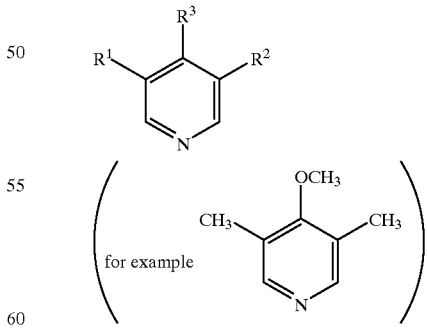

$R^1$, $R^2$ and $R^3$ as previously defined, with a radical • aryloxycarbonyl under free radical reaction conditions or obvious chemical equivalent.

According to another aspect of the invention, there is provided a process of forming a compound having the structure

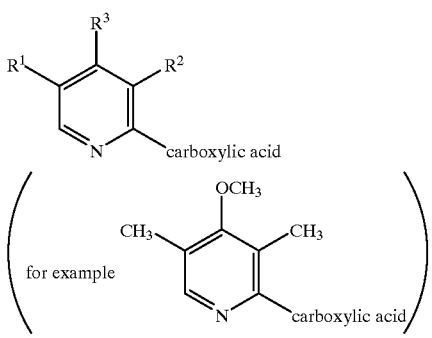

by reacting a compound having the structure

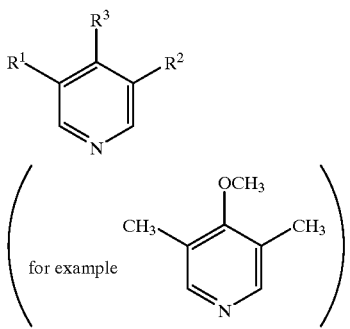

$R^1$, $R^2$ and $R^3$ as previously defined, with a radical • carboxylic acid under free radical reaction conditions or obvious chemical equivalent.

According to another aspect of the invention, there is provided a process of forming a compound having the structure

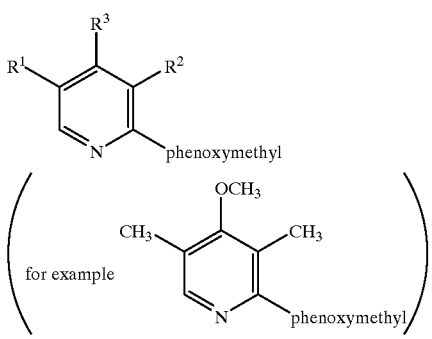

by reacting a compound having the structure

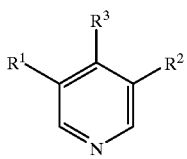

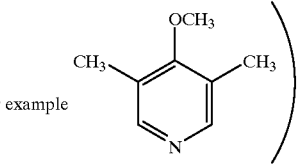

$R^1$, $R^2$ and $R^3$ as previously defined, with a radical • phenoxymethyl under free radical reaction conditions or obvious chemical equivalent.

According to another aspect of the invention, there is provided a process of forming a compound having the structure hydroxymethyl pyridine structure (for example with OCH₃, CH₃ substituents and hydroxymethyl group) by reacting a compound having the structure pyridine structure (for example with OCH₃ and CH₃ substituents)

$R^1$, $R^2$ and $R^3$ as previously defined, with a radical • hydroxymethyl under free radical reaction conditions or obvious chemical equivalent.

The inventors propose that their approach would be highly suitable for use to make pyridines which are intermediates that could be used to make medicines.

Applicants propose as exemplary of their invention that the following pyridine compound:

I pyridine structure with $R^1$, $R^2$, $R^3$ substituents and CH₂R group at position 2 wherein
$R^1$=H or $CH_3$
$R_2$=H or $CH_3$
$R^3$=Alkoxy (1–4C), $OCH_2CF_3$, Cyano, Hydrogen, Halogen, Acetoxy or Aryloxy, any electron withdrawing group or salts (organic or inorganic) of electron donating groups R=Alkoxy, Hydroxy, Halogen, Activated ester, Tosylate, Mesylate, Thiol, or Xanthyl be prepared by the following schemes of reaction (in suitable solvents):

Scheme 1:

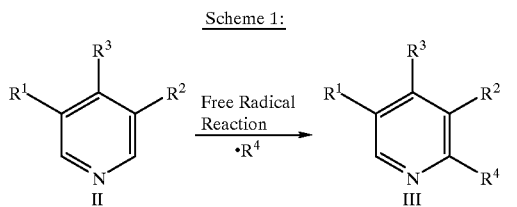

wherein formula II or III:
$R^1$, $R^2$, $R^3$ are the same as specified in formula I
$R^4$=Alkyl, Acyl (ketone), Amides (carbamoyl), Alkoxycarbonyl (COOR', R'=(1–3C)), Aryloxycarbonyl, Carboxylic acid, Phenoxymethyl, Hydroxymethyl.

Compound I may then be manufactured using intermediate III.

For the synthesis of an intermediate useful in the manufacture of Omeprazole, the following substituents appear on the intermediate of formula I' where $R^1=R^2=CH_3$; $R^3=OCH_3$, R=Cl. An exemplary process of manufacture may be characterized by the following steps: (Scheme 2)

a) Functionalization of the 4-position: Reacting a compound of the formula II, where $R^3$=H with a halogenating agent, examples include thionyl halide, phosphorous oxyhalide, or phosphorous pentahalide.

b) Functionalization of the 2 position: Reacting the 4-halopyridine with an organic free radical comprised of the $R^4$ groups specified above, preferably the alkoxycarbonyl.

c) Nucleophilic substitution of the Halogen group at the 4-position by an —$OCH_3$ radical.

d) Reduction of the $R^4$ group to prepare a compound of the formula I, where R corresponds to an OH group.

e) Nucleophilic substitution of the OH radical by a Cl radical using $SOCl_2$ or any other halogenating agent.

The above sequence is a preferred; however, step d could be performed before step c. The steps may be carried out in different orders as would be understood by persons skilled in the art. It is preferred to have an electron withdrawing group at the 4-position before functionalizing the 2-position.

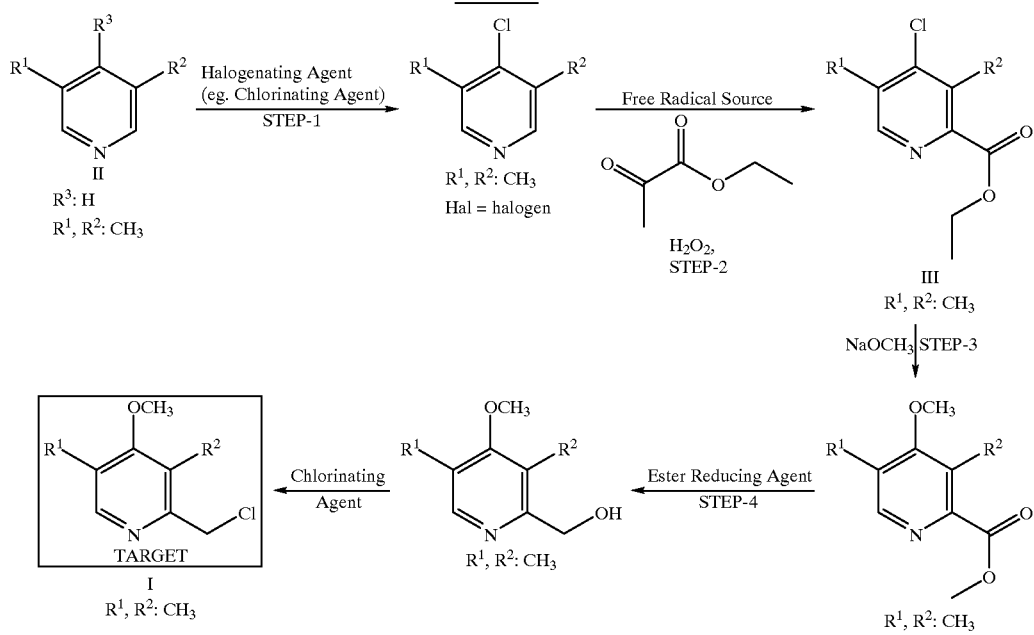

Several alkoxycarbonyl radical sources can be used: (see e.g. Tet. Lett. 1973, 645)

For example:
a) Redox decomposition of oxyhydroperoxides of (α-ketoesters (Scheme-2),
b) Oxidative decarboxylation of semiesters of oxalic acid by peroxydisulfate or lead tetraacetate,
c) Hydrogen abstraction from alkyl formates.

Method in subparagraph (a) is the preferred method because it provides simple conditions and good yields.

According to another aspect of the invention, there is provided a process of reacting a compound of formula II

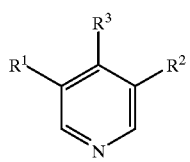

II wherein $R^1$=H or $CH_3$ $R^2$=H or $CH_3$ $R^3$ is hydrogen with $SOCl_2$ any other halogenating agent to form 4-halopyridine derivatives.

In one embodiment the halogenating agent can be used neat, and in another embodiment it can be used in the presence of solvents such as toluene, xylene, chlorobenzene or any other suitable inert solvent. Preferably the reaction occurs substantially solvent free.

The following is a list of the substituents R, $R^2$, $R^3$, $R^4$, $R^5$, on Formula I, that correspond to the substituents on the medicines:

| $R^1$ | $R^2$ | R | $R^3$ | Precursor for |
|---|---|---|---|---|
| $CH_3$ | $CH_3$ | (benzimidazole-S- with $OCH_3$) | $OCH_3$ | Omeprazole |
| H | $CH_3$ | (benzimidazole-S- with $OCH_2F$) | $OCH_3$ | Pantoprazole |
| H | $CH_3$ | (benzimidazole-S-) | $OCH_2CF_3$ | Lansoprazole |

The invention will now be illustrated with reference to the following examples of manufacture:

EXAMPLE 1

Synthesis of 4-Chloro-3,5-dimethylpyridine 3,5-Dimethylpyridine (1 eq.) was added dropwise to thionyl chloride (1–5 eq.); either neat or in a solvent (2–10 volumes), (such as toluene, 4-chlorobenzene, xylene etc.) at a temperature ranging from 0–70° C. At the end of the addition the mixture was heated to reflux for 12–20 hours. At the end of the reaction the solvent (1–5 volumes) was added (if not already present). A fraction of the solvent was distilled to get rid of the excess thionyl chloride. The precipitated solid was filtered, washed with toluene followed by methanol, a brown solid was obtained. The crude product was dissolved in hot methanol, treated with charcoal, filtered over celite, cooled to room temperature and then to 0–5° C. and allowed to crystallize. 4-Chloro-3,5-dimethyl pyridine. HCl was obtained in over 70% yields.

Another work-up method: At the end of the reaction, the mixture was allowed to cool down to room temperature and an organic solvent such as toluene (1–5 vol.) was added (if not already present), followed by dropwise addition of an aqueous NaOH solution until pH=9–11. The phases were separated and the toluene was evaporated to produce 4-Chloro-3, 5-dimethylpyridine in the free base form.

Also, the mode of addition could be reversed with no effect on the yield, i.e., thionyl chloride addition to 3,5-dimethylpyridine.

EXAMPLE 2

Synthesis of 2-Pyridinecarboxylic acid, 4-chloro-3, 5-dimethyl-, ethyl ester

Ethyl pyruvate (0.9–3 eq.) was stirred and cooled (−20−+0° C.) and hydrogen peroxide (30–35%, 0.9–3 eq) was added dropwise. This solution and a solution of Iron sulfate heptahydrate (0.9–3 eq.) in water (1–5 vol.) were then slowly and simultaneously added dropwise into a stirred solution of 4-Chloropyridine (1 eq) in water (1–5 vol.) and conc. $H_2SO_4$ (1–4 eq.) and Toluene (0–20 vol.), keeping the temperature below 25° C. The mixture was then stirred at room temperature until the reaction is judged complete. The mixture was poured into ice cold NaOH (10%) solution. Toluene (2–5 vol.) was added (If not already present), the layers were separated. The toluene layer was washed with 0.5 N HCl solution and evaporated to yield the crude 2-Pyridinecarboxylic acid, 4-chloro-3,5-dimethyl-, ethyl ester in over 90% yield based on the consumed starting material and over 50% isolated yield.

The starting material present in the aqueous layer was free based and recycled.

EXAMPLE 3

Pyridinecarboxylic acid, 3,5-dimethyl-4-methoxy-methyl ester

A solution of the crude Pyridinecarboxylic acid, 4-chloro-3,5-dimethyl-, ethyl ester (1 eq.) in methanol (3–10 vol.)

was added freshly prepared sodium methoxide (2–5 eq.). The mixture was heated under reflux for 5–12 hours. Methanol was evaporated and substituted with toluene. Water was added and the layers were separated. Toluene was evaporated to yield the crude Pyridinecarboxylic acid, 3,5-dimethyl-4-methoxy-, methyl ester in over 75% yield.

EXAMPLE 4

3,5-dimethyl-2-hydroxymethyl-4-methoxypyridine

The crude Pyridinecarboxylic acid, 3,5-dimethyl-4-methoxy-, methyl ester (1 eq.) was dissolved in toluene (3–10 vol.). The solution was stirred under a nitrogen atmosphere and diisobutylaluminum hydride (neat or in toluene) (2–3 eq.) was added dropwise keeping the temperature between (+10 to- +25° C.). At the end of the addition the reaction was stirred at room temperature for 30 minutes and then it was heated to 50–60° C. 1 hour, or until the reaction was judged complete. At the end of the reaction the excess diisobutylaluminum hydride was quenched with ethyl acetate. An aqueous base solution (such as 20% NaOH) was added and the layers were separated. The toluene layer was evaporated to yield the crude 3,5-dimethyl-2-hydroxymethyl-4-methoxypyridine in over 85% yield.

Other specific intermediate (I) compounds can be prepared by persons skilled in the art having regard to the teachings herein.

Thus, as many changes can be made to the examples without departing from the scope of the invention, it is intended that all material contained herein be interpreted as illustrative of the invention and not in a limiting sense.

What is claimed is:

1. A process of preparing a drug selected from the group consisting of omeprazole lanzoprazole and pantoprazole, comprising reacting a compound of the formula II

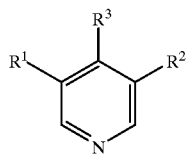

II under free radical reaction conditions with a radical $R^4$ to form a compound of formula III

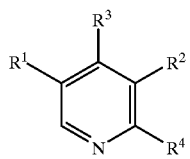

III wherein
  $R^1$=H or $CH_3$
  $R^2$=H or $CH_3$
  $R^3$=Alkoxy (1–4C), $OCH_2CF_3$, Cyano, Hydrogen, Halogen, Acetoxy or Aryloxy, any electron withdrawing group or salts (organic or inorganic) of electron donating groups
  $R^4$=Alkyl, Acyl, Amides, Alkoxycarbonyl, Aryloxycarbonyl, Carboxylic Acid, Phenoxymethyl, or Hydroxymethyl and further reacting compound III to form the drug.

2. A process of producing a compound of formula I'

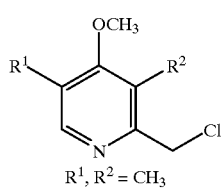

I' by carrying out the following reaction steps

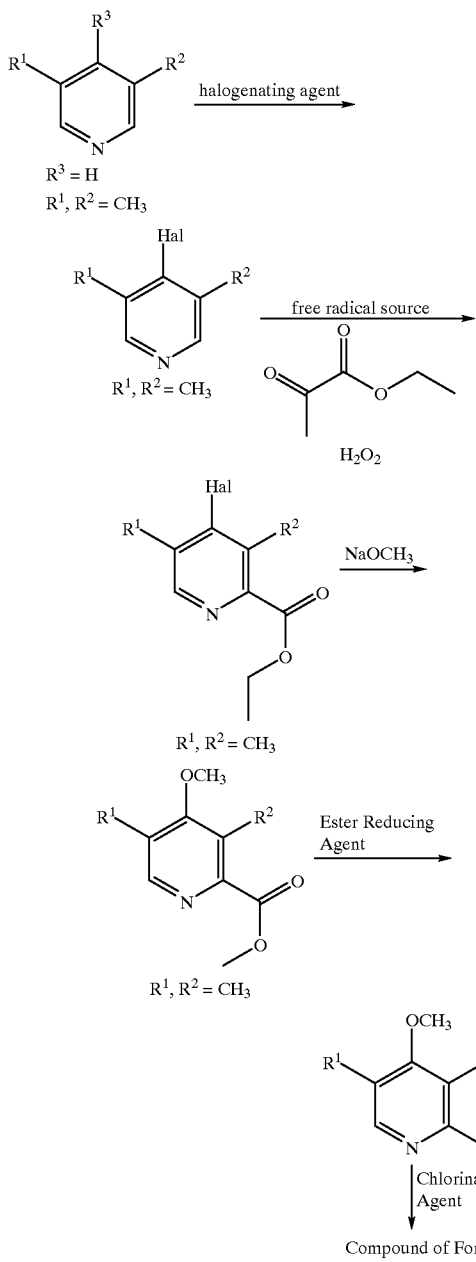

3. A process of manufacturing Omeprazole by using the intermediate with the appropriate substituents formed by the process as claimed in claim 1 or 2.

4. A process of manufacturing Pantoprazole by using the intermediate with the appropriate substituents formed by the process as claimed in claim 1 or 2.

5. A process of manufacturing Lansoprazole by using the intermediate with the appropriate substituents formed by the process as claimed in claim 1 or 2.

6. A process of forming a compound having the structure

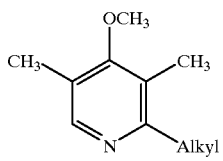

by reacting a compound having the structure

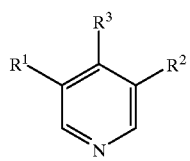

wherein $R^1$=H or $CH_3$ $R^2$=H or $CH_3$ $R^3$=Alkoxy (1–4C), $OCH_2CF_3$, Cyano, Hydrogen, Halogen, Acetoxy or Aryloxy, any electron withdrawing group or salts (organic or inorganic) of electron donating groups with a radical • alkyl under free radical reaction conditions.

7. A process of forming a compound having the structure

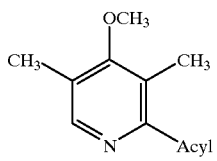

by reacting a compound having the structure

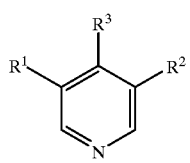

wherein $R^1$=H or $CH_3$ $R^2$=H or $CH_3$ $R^3$=Alkoxy (1–4C), $OCH_2CF_3$, Cyano, Hydrogen, Halogen, Acetoxy or Aryloxy, any electron withdrawing group or salts (organic or inorganic) of electron donating groups with a radical • acyl under free radical reaction conditions.

8. A process of forming a compound having the structure

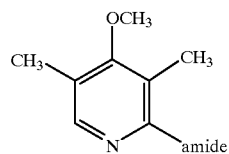

by reacting a compound having the structure

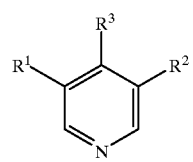

wherein $R^1$=H or $CH_3$ $R^2$=H or $CH_3$ $R^3$=Alkoxy (1–4C), $OCH_2CF_3$, Cyano, Hydrogen, Halogen, Acetoxy or Aryloxy, any electron withdrawing group or salts (organic or inorganic) of electron donating groups with a radical • amide under free radical reaction conditions.

9. A process of forming a compound having the structure

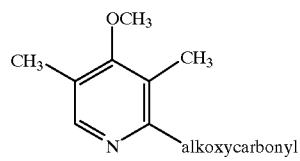

by reacting a compound having the structure

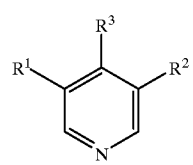

wherein $R^1$=H or $CH_3$ $R^2$=H or $CH_3$ $R^3$=Alkoxy (1–4C), $OCH_2CF_3$, Cyano, Hydrogen, Halogen, Acetoxy or Aryloxy, any electron withdrawing group or salts (organic or inorganic) of electron donating groups with a radical • alkoxycarbonyl under free radical reaction conditions.

10. A process of forming a compound having the structure

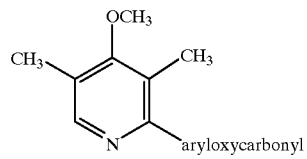

by reacting a compound having the structure

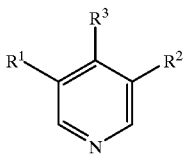

wherein

R¹=H or CH₃

R²=H or CH₃

R³=Alkoxy (1–4C), OCH₂CF₃, Cyano, Hydrogen, Halogen, Acetoxy or Aryloxy, any electron withdrawing group or salts (organic or inorganic) of electron donating groups with a radical • aryloxycarbonyl under free radical reaction conditions.

11. A process of forming a compound having the structure

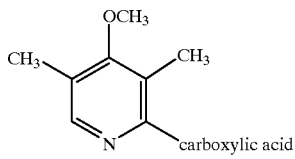

by reacting a compound having the structure

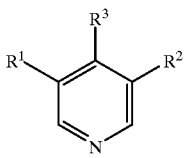

wherein

R¹=H or CH₃

R²=H or CH₃

R³=Alkoxy (1–4C), OCH₂CF₃, Cyano, Hydrogen, Halogen, Acetoxy or Aryloxy, any electron withdrawing group or salts (organic or inorganic) of electron donating groups with a radical • carboxylic acid under free radical reaction conditions.

12. A process of forming a compound having the structure

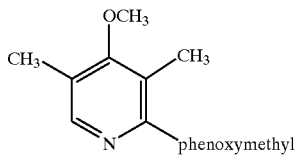

by reacting a compound having the structure

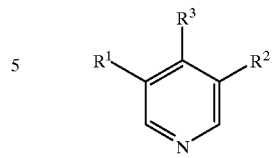

wherein

R¹=H or CH₃

R²=H or CH₃

R³=Alkoxy (1–4C), OCH₂CF₃, Cyano, Hydrogen, Halogen, Acetoxy or Aryloxy, any electron withdrawing group or salts (organic or inorganic) of electron donating groups with a radical • phenoxymethyl under free radical reaction conditions.

13. A process of forming a compound having the structure

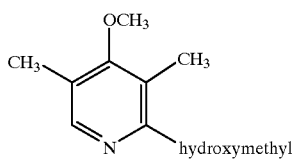

by reacting a compound having the structure

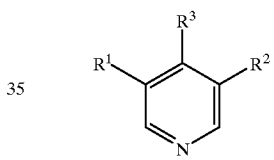

wherein

R¹=H or CH₃

R²=H or CH₃

R³=Alkoxy (1–4C), OCH₂CF₃, Cyano, Hydrogen, Halogen, Acetoxy or Aryloxy, any electron withdrawing group or salts (organic or inorganic) of electron donating groups with a radical • hydroxymethyl under free radical reaction conditions.

14. A compound of formula III

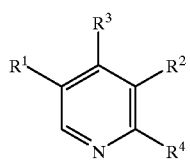

III wherein

R¹=H or CH₃

R²=H or CH₃

R³=Alkoxy (1–4C), OCH₂CF₃, Cyano, Hydrogen, Halogen, Acetoxy or Aryloxy, any electron withdrawing group or salts (organic or inorganic) of electron donating groups $R^4$=Alkyl, Acyl (ketone), Amides (carbamoyl), Alkoxycarbonyl (COOR$^1$, R$^1$=(1–3C)), Aryloxycarbonyl, Carboxylic Acid, Phenoxymethyl, Hydroxymethyl.

15. A process of reacting a compound of formula II

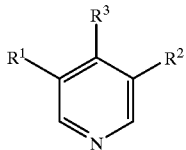

wherein
$R^1$=H or CH$_3$
$R^2$=H or CH$_3$
$R^3$ is hydrogen
with SOCl$_2$ or any other halogenating agent to form 4-halopyridine derivatives.

16. The process of claim 15 wherein said process occurs in the presence of a suitable solvent.

17. The process of claim 16 wherein said suitable solvent is selected from the group consisting of toluene, xylene, chlorobenzene or any other inert solvent.

18. The process of claim 15 wherein said process occurs substantially free of any solvent.

19. The process of claim 1 wherein R$^4$ is alkyl.

20. The process of claim 1 wherein R$^4$ is acyl.

21. The process of claim 1 wherein R$^4$ is an amide.

22. The process of claim 1 wherein R$^4$ is alkoxycarbonyl.

23. The process of claim 1 wherein R$^4$ is aryloxycarbonyl.

24. The process of claim 1 wherein R$^4$ is carboxylic acid.

25. The process of claim 1 wherein R$^4$ is phenoxymethyl.

26. The process of claim 1 wherein R$^4$ is hydroxymethyl.

27. The process of claim 20 wherein said acyl is a ketone.

28. The process of claim 21 where said amide is a carbamoyl.

29. The process of claim 22 wherein said alkoxycarbonyl is COOR$^1$ and wherein said R$^1$=1–3C.

* * * * *